United States Patent
Beausoleil et al.

(10) Patent No.: US 6,592,554 B2
(45) Date of Patent: Jul. 15, 2003

(54) CATHETER HOLDING SYSTEM

(76) Inventors: Annette A. Beausoleil, 548 Galway Dr., Burlington, Ontario L7L 2S7 (CA); Frank F. Kelly, 548 Galway Dr., Burlington, Ontario L7L 2S7 (CA)

( * ) Notice: Subject to any disclaimer, the term of this patent is extended or adjusted under 35 U.S.C. 154(b) by 0 days.

(21) Appl. No.: 09/728,838

(22) Filed: Dec. 1, 2000

(65) Prior Publication Data

US 2002/0068903 A1 Jun. 6, 2002

(51) Int. Cl.⁷ ................................................ A61M 5/32
(52) U.S. Cl. ...................................................... 604/174
(58) Field of Search ................................ 604/174, 179, 604/180; 2/94; 128/869

(56) References Cited

U.S. PATENT DOCUMENTS

| | | | |
|---|---|---|---|
| 4,333,468 A | | 6/1982 | Geist |
| 4,404,687 A | * | 9/1983 | Hager ............................. 2/93 |
| 4,484,914 A | | 11/1984 | Brown |
| 4,666,432 A | * | 5/1987 | McNeish et al. ........... 604/174 |
| 4,822,342 A | * | 4/1989 | Brawner ..................... 604/180 |
| 5,496,282 A | * | 3/1996 | Millitzer et al. ............ 604/179 |
| 5,702,371 A | * | 12/1997 | Bierman ..................... 604/180 |
| D389,581 S | | 1/1998 | Fein |
| 5,776,106 A | | 7/1998 | Matyas |
| 6,000,402 A | * | 12/1999 | Able .......................... 128/869 |

* cited by examiner

*Primary Examiner*—Henry Bennett
*Assistant Examiner*—Sabrina Dagostino

(57) ABSTRACT

A catheter holding system for receiving and holding a standard catheter in place to ensure it works properly. The catheter holding system includes a pocket that includes a front panel and a rear panel; the front panel is secured to the rear panel of the pocket. The front panel and the rear panel of the pocket defines an interior space such that the interior space of the pocket is adapted for holding a catheter.

3 Claims, 2 Drawing Sheets

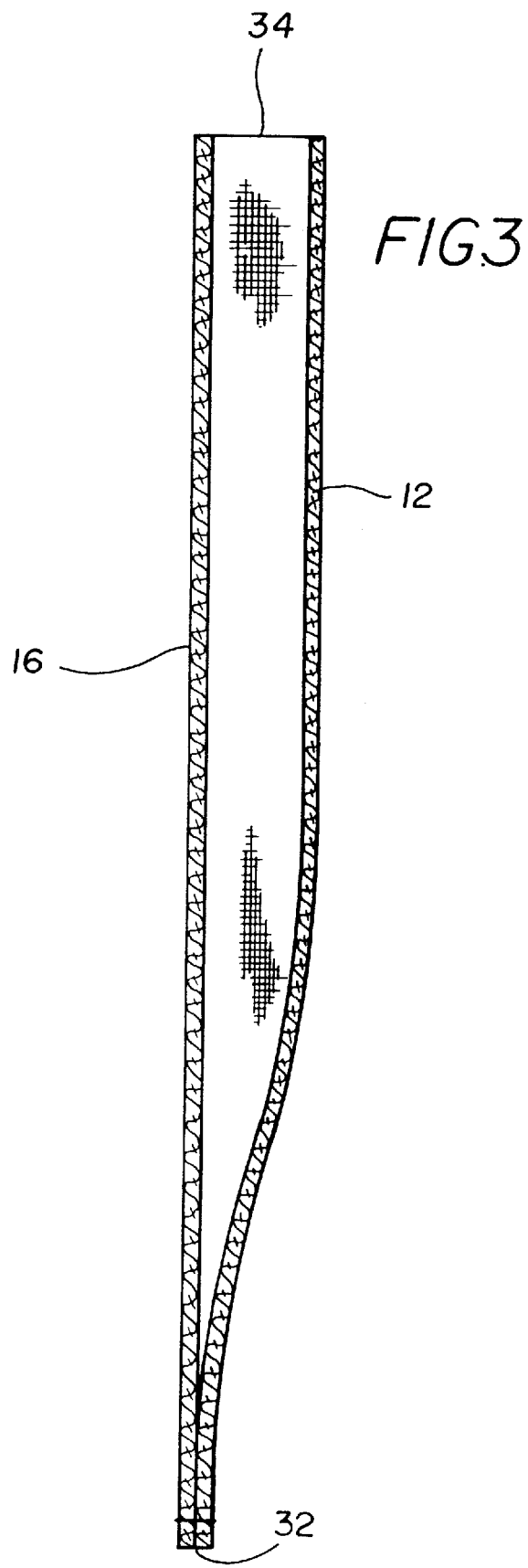

CATHETER HOLDING SYSTEM

BACKGROUND OF THE INVENTION

1. Field of the Invention

The present invention relates to catheter holding systems and more particularly pertains to a new catheter holding system for receiving and holding a standard catheter in place to ensure it works properly.

2. Description of the Prior Art

The use of catheter holding systems is known in the prior art. More specifically, catheter holders heretofore devised and utilized are known to consist basically of familiar, expected and obvious structural configurations, notwithstanding the myriad of designs encompassed by the crowded prior art which have been developed for the fulfillment of countless objectives and requirements.

Known prior art includes U.S. Pat. No. 5,702,371; U.S. Pat. No. 5,776,106; U.S. Pat. No. 4,333,468; U.S. Pat. No. Des. 389,581; U.S. Pat. No. 4,484,914; and U.S. Pat. No. 4,822,342.

While these devices fulfill their respective, particular objectives and requirements, the aforementioned patents do not disclose a new catheter holding system. The inventive device includes a pocket that includes a front panel and a rear panel. The front panel is secured to the rear panel of the pocket. The front panel and the rear panel of the pocket define an interior space such that the interior space of the pocket is adapted for holding a catheter.

In these respects, the catheter holding system according to the present invention substantially departs from the conventional concepts and designs of the prior art, and in so doing provides an apparatus primarily developed for the purpose of receiving and holding a standard catheter in place to ensure it works properly.

SUMMARY OF THE INVENTION

In view of the foregoing disadvantages inherent in the known types of catheter holders now present in the prior art, the present invention provides a new catheter holding system construction wherein the same can be utilized for receiving and holding a standard catheter in place to ensure it works properly.

The general purpose of the present invention, which will be described subsequently in greater detail, is to provide a new catheter holding system apparatus and method which has many of the advantages of the catheter holders mentioned heretofore and many novel features that result in a new catheter holding system which is not anticipated, rendered obvious, suggested, or even implied by any of the prior art catheter holders, either alone or in any combination thereof.

To attain this, the present invention generally comprises a pocket that includes a front panel and a rear panel; the front panel is secured to the rear panel of the pocket. The front panel and the rear panel of the pocket defines an interior space such that the interior space of the pocket is adapted for holding a catheter.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new catheter holding system apparatus and method which has many of the advantages of the catheter holders mentioned heretofore and many novel features that result in a new catheter holding system which is not anticipated, rendered obvious, suggested, or even implied by any of the prior art catheter holders, either alone or in any combination thereof.

It is another object of the present invention to provide a new catheter holding system, which may be easily and efficiently manufactured and marketed.

It is a further object of the present invention to provide a new catheter holding system, which is of a durable and reliable construction.

An even further object of the present invention is to provide a new catheter holding system which is susceptible of a low cost of manufacture with regard to both materials and labor, and which accordingly is then susceptible of low prices of sale to the consuming public, thereby making such catheter holding system economically available to the buying public.

Still yet another object of the present invention is to provide a new catheter holding system which provides in the apparatuses and methods of the prior art some of the advantages thereof, while simultaneously overcoming some of the disadvantages normally associated therewith.

Still another object of the present invention is to provide a new catheter holding system for receiving and holding a standard catheter in place to ensure it works properly.

Yet another object of the present invention is to provide a new catheter holding system which includes a pocket that includes a front panel and a rear panel, the front panel is secured to the rear panel of the pocket. The front panel and the rear panel of the pocket defines an interior space such that the interior space of the pocket is adapted for holding a catheter.

Still yet another object of the present invention is to provide a new catheter holding system that is of lightweight and comfortable design that reduces the amount of adhesives used, eliminating irritation. The present invention eliminated dangling tubes, keeping them from being pulled or snagged.

Even still another object of the present invention is to provide a new catheter holding system that reduces frequency with which catheters must be repositioned or retaped, which fosters independence and limits embarrassment from needing assistance to retape the catheter.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 3 is a side view of the present invention.

DESCRIPTION OF THE PREFERRED EMBODIMENT

Figure 1:
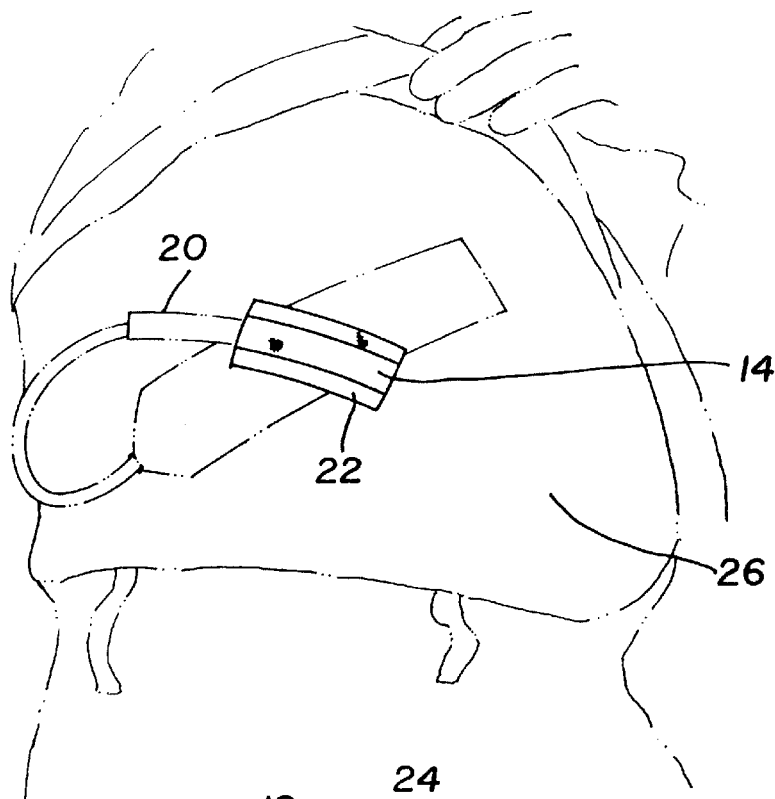
FIG. 1 is a perspective view of a new catheter holding system according to the present invention.
Figure 2:
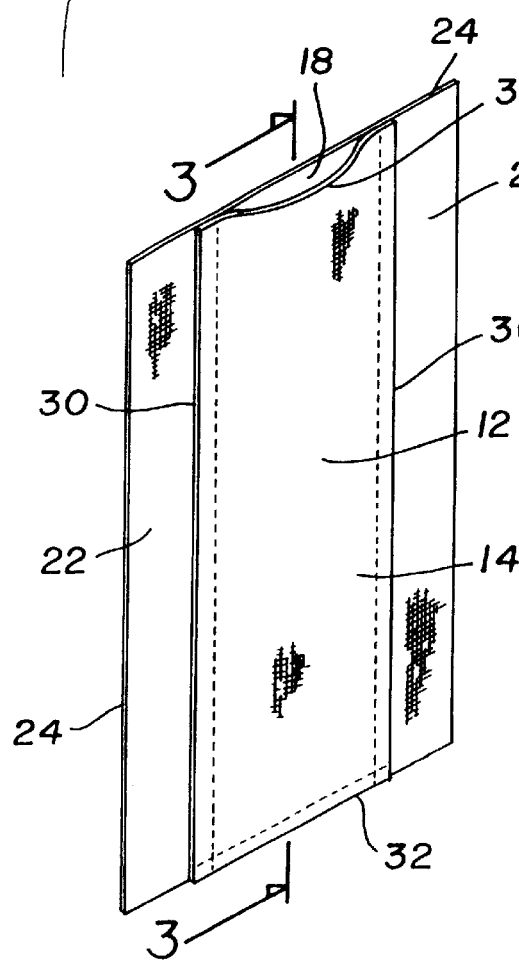
FIG. 2 is a front perspective view of the present invention.

With reference now to the drawings, and in particular to FIGS. 1 through 3 thereof, a new catheter holding system embodying the principles and concepts of the present invention and generally designated by the reference numeral 10 will be described.

As best illustrated in FIGS. 1 through 3, the catheter holding system 10 generally comprises a pocket 12 that includes a front panel 14 and a rear panel 16, the front panel 14 is secured to the rear panel 16 of the pocket 12. The front panel 14 and the rear panel 16 of the pocket 12 defines an interior space 18 such that the interior space 18 of the pocket 12 is designed for holding a catheter 20.

The rear panel 16 of the pocket 12 has pair of flaps 22, one of each of the flaps 22 extends outwardly from an adjacent side of the front panel 14. Tape 24 is provided for coupling the flaps 22 to the skin 26 of a user such that the tape 24 anchors the pocket 12 to the skin 26.

The front panel 14 is coupled to the rear panel 16 along a pair of side edges 30 and an end edge 32 such that the side edges 30 and the end edge 32 define the interior space 18 of the pocket 12. The interior space 18 has an open end 34 for accessing the interior space 18 of the pocket 12. The front panel 14 has top edge 36, the top edge 36 has a length greater than a length of the rear panel 16 between the side edges 30 when the side edges 30 are coupled to the rear panel 16 such that the top edge 36 is in an open position. The front panel 14 and the rear panel 16 are made of a washable material such as cotton or nylon. In an embodiment, the material may be elastic and the pocket interior sized slightly less than the area of the catheter such that the pocket stretches to receive the catheter, thus facilitating holding of the catheter in the pocket.

In use, a user would position the pocket on the side of body of a patient and fasten the tape flaps to the body. The catheter then easily slips in and out of the pocket with the proper amount for tension to hold the catheter tube in position.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

We claim:

1. A catheter holding system comprising:

a catheter;

a pocket having a front panel and a rear panel, said front panel being secured to said rear panel of said pocket;

said front panel and said rear panel of said pocket defining an interior space such that said interior space of said pocket is for holding a catheter;

wherein said rear panel of said pocket has a pair of flaps, one of each of said flaps extending outwardly from an adjacent side of said front panel, a plurality of tape members being for adhering said flaps to the skin of a user such that for securing said pocket to the user;

wherein said front panel is coupled to said rear panel along a pair of side edges and an end edge such that said side edges and said end edge define said interior space of said pocket, said interior space having a open end for accessing said interior space of said pocket;

wherein said front panel has top edge, said top edge having a length greater than a length of said rear panel between said side edges when said side edges are coupled to said rear panel such that a portion of said top edge of said front panel is held in an arched configuration away from said rear panel into an open position; and wherein said front panel and said rear panel are made of a washable material.

2. The catheter holding system as set forth in claim 1, wherein said washable material comprises a cotton material.

3. The catheter holding system as set forth in claim 1, wherein said washable material comprises a nylon material.

* * * * *